(12) United States Patent
Volkar

(10) Patent No.: US 12,311,158 B2
(45) Date of Patent: May 27, 2025

(54) PATIENT LINE AIR DETECTION AND REUSE PREVENTION

(71) Applicant: BAYER HEALTHCARE LLC, Whippany, NJ (US)

(72) Inventor: John Volkar, Valencia, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 582 days.

(21) Appl. No.: 17/639,641

(22) PCT Filed: Sep. 2, 2020

(86) PCT No.: PCT/US2020/048993
§ 371 (c)(1),
(2) Date: Mar. 2, 2022

(87) PCT Pub. No.: WO2021/046082
PCT Pub. Date: Mar. 11, 2021

(65) Prior Publication Data
US 2022/0288328 A1    Sep. 15, 2022

Related U.S. Application Data

(60) Provisional application No. 62/894,988, filed on Sep. 3, 2019.

(51) Int. Cl.
*A61M 5/50* (2006.01)
*A61M 5/14* (2006.01)
*A61M 5/145* (2006.01)

(52) U.S. Cl.
CPC ........ *A61M 5/5086* (2013.01); *A61M 5/1407* (2013.01); *A61M 5/1452* (2013.01);
(Continued)

(58) Field of Classification Search
CPC .............. A61M 5/5086; A61M 5/1407; A61M 2005/16863; A61M 2005/16868;
(Continued)

(56) References Cited

U.S. PATENT DOCUMENTS 766,169 A    8/1904   Christiansen
3,608,555 A *  9/1971  Greyson ................. A61L 29/18
                                         250/519.1
(Continued)

FOREIGN PATENT DOCUMENTS

WO    2017040152 A1    3/2017
WO    2018144369 A1    8/2018

OTHER PUBLICATIONS

"International Preliminary Report on Patentability from PCT Application No. PCT/US2020/048993", Mar. 17, 2022.

*Primary Examiner* — Nilay J Shah
(74) *Attorney, Agent, or Firm* — James R. Stevenson; Alexandria Quezada

(57) ABSTRACT

An administration line for use with a fluid injector system includes a fluid verification module configured to be in operative communication with a housing of the fluid injector system such that the fluid injector system can determine a status of the administration line. The fluid verification module includes a body defining an inlet port, an outlet port, and a fluid channel extending from the inlet port to the outlet port; a first tubing section connected to the inlet port; and a second tubing section connected to the outlet port.

16 Claims, 12 Drawing Sheets

(52) U.S. Cl.
CPC . *A61M 2005/1402* (2013.01); *A61M 2205/14* (2013.01); *A61M 2205/273* (2013.01); *A61M 2205/3569* (2013.01); *A61M 2205/584* (2013.01); *A61M 2205/587* (2013.01)

(58) Field of Classification Search
CPC .... A61M 2005/16872; A61M 5/16854; A61M 5/16859
See application file for complete search history.

(56) References Cited

U.S. PATENT DOCUMENTS

| | | | |
|---|---|---|---|
| 3,923,060 A * | 12/1975 | Ellinwood, Jr. | A61B 5/021 128/DIG. 13 |
| 4,366,384 A * | 12/1982 | Jensen | A61M 5/365 250/575 |
| 5,383,858 A | 1/1995 | Reilly et al. | |
| 5,496,273 A | 3/1996 | Pastrone et al. | |
| 5,989,222 A * | 11/1999 | Cole | A61M 5/16854 604/151 |
| 7,553,294 B2 | 6/2009 | Lazzaro et al. | |
| 8,945,051 B2 | 2/2015 | Schriver et al. | |
| 10,022,493 B2 | 7/2018 | Shearer, Jr. et al. | |
| 10,507,319 B2 | 12/2019 | Haury et al. | |
| 2005/0234428 A1 * | 10/2005 | Spohn | A61M 5/007 604/533 |
| 2011/0152757 A1 | 6/2011 | Beck et al. | |
| 2016/0317762 A1 * | 11/2016 | Kimm | A61M 5/5086 |

* cited by examiner

PATIENT LINE AIR DETECTION AND REUSE PREVENTION

CROSS-REFERENCE TO RELATED APPLICATION

The present application is a U.S. national phase application under 35 U.S.C. § 371 of PCT International Application No. PCT/US2020/048993, filed Sep. 2, 2020 and claims the benefit of U.S. Provisional Patent Application No. 62/894,988, filed Sep. 3, 2019, the disclosures of which is are hereby incorporated by reference in their entirety.

BACKGROUND

Field of Disclosure

The present disclosure relates to fluid injector systems, and more particularly to fluid injector systems including administration line assemblies having features to increase patient safety such as air detection and/or reuse prevention features.

Description of Related Art

In many medical diagnostic and therapeutic procedures, a medical practitioner, such as a physician, injects a patient with one or more medical fluids. In recent years, a number of medical fluid delivery systems for pressurized injection of fluids, such as a contrast solution (often referred to simply as "contrast"), a flushing agent (such as saline), and other medical fluids, have been developed for use in procedures such as angiography, computed tomography (CT), ultrasound, magnetic resonance imaging (MRI), positron emission tomography (PET), and other molecular imaging procedures.

In some injection procedures, the medical practitioner places a catheter or needle into a vein or artery of the patient. The catheter or needle is connected to the medical fluid delivery system by way of a tubing set. The tubing sets often include features (such as check valves) in their design which protect the fluid source from blood-born contamination. Such tubing sets are designed and recommended for a finite number of uses, typically one—in order to prevent cross-contamination of the remainder of the system between patients. However, due to accidental or purposeful misuse, tubing sets may be used for more than the recommended number of uses.

Another limitation of conventional patient lines is that priming is often clumsy and potentially unhygienic. Priming the patient line with fluid, which is necessary to prevent injection of air into the patient, is achieved by injecting fluid through the patient line prior to connecting the line to the patient. To catch and contain fluid expelled from the patient line during priming, practitioners often hold the end of the patient line over a waste receptacle or cloth. This practice, however, has the potential to result in contamination of the sterile tip of the line.

SUMMARY OF THE DISCLOSURE

In view of the foregoing, there exists a need for patient lines and fluid delivery systems that enforce the recommended replacement schedule of the patient lines. Additionally, there exists a need for patient lines having features to facilitate hygienic priming. Against this background, aspects or examples of the present disclosure are directed to an administration line for administration line for use with a fluid injector system. In some aspects or examples, the administration line includes a fluid verification module configured to be in operative communication with a housing of the fluid injector system such that the fluid injector system can determine a status of the administration line. The fluid verification module includes a body defining an inlet port, an outlet port, and a fluid channel extending from the inlet port to the outlet port; a first tubing section connected to the inlet port; and a second tubing section connected to the outlet port.

In some aspects or examples, the first tubing section includes a first inlet fitting configured for connection to a first fluid reservoir of the fluid injector system, and a second inlet fitting configured for connection to a second fluid reservoir of the fluid injector system. The first inlet fitting is configured to connect to the second inlet fitting during storage or shipment of the administration line.

In some aspects or examples, the first tubing section includes an inlet fitting configured for connection to an intermediate tubing set in fluid communication with at least one fluid reservoir of the fluid injector system. The inlet fitting is configured to connect to the body of the fluid verification module during storage or shipment of the administration line.

In some aspects or examples, the body further defines a priming port, and the second tubing section includes an outlet fitting configured to connect to the priming port during storage or shipment of the administration line.

In some aspects or examples, the priming port is in fluid communication with a priming cavity, and the priming cavity is configured to receive and hold priming fluid from the outlet fitting during a priming operation of the administration line.

In some aspects or examples, the administration line further includes at least one sheet material disposed within the priming cavity. The at least one sheet material includes a first sheet material having indicia, and a second sheet material which transitions from an opaque state to an at least partially translucent state when the second sheet material is contacted by the priming fluid. The indicia on the first sheet material is obstructed by the second sheet material when the second sheet material is in the opaque state. The indicia on the first sheet material is visible via a window in the body when the second sheet material is in the translucent state.

In some aspects or examples, the administration line further includes at least one sheet material disposed within the priming cavity. The at least one sheet material is configured to change in electrical resistance when contacted by the priming fluid. When the fluid verification module is mounted to the housing of the fluid injector system, the at least one sheet material is configured to interface with at least one probe of the fluid injector system for measuring electrical resistance of the at least one sheet material.

In some aspects or examples, the body of the fluid verification module further includes a capillary channel in fluid communication with the priming cavity and configured to take up at least a portion of the priming fluid via capillary action.

In some aspects or examples, at least a portion of the body of the fluid verification module is configured to act as a lens to display light emitted from a light source of the fluid injector system.

In some aspects or examples, the body of the fluid verification module includes one or more engagement features configured for securing the fluid verification module to the housing of the fluid injector system.

In some aspects or examples, the fluid channel is at least partially transparent such that an imaging device of the housing can determine the presence or absence of fluid in the fluid channel.

In some aspects or examples, the fluid channel is flexible and configured to interface with a strain gauge of the housing such that the strain gauge can determine fluid pressure in the administration line.

In some aspects or examples, the administration line further includes at least one of an inlet one-way valve associated with the inlet port and an outlet one-way valve associated with the outlet port. At least one of the inlet one-way valve and the outlet one-way valve prohibit fluid flow in an upstream direction from the second tubing section toward the first tubing section.

Other aspects or examples of the present disclosure are directed to a fluid injector system configured to perform an injection procedure in connection with a diagnostic imaging procedure. The fluid injector system includes an administration line including a fluid verification module. The fluid verification module includes a body defining an inlet port, an outlet port, and a fluid channel extending from the inlet port to the outlet port. The administration line further includes a first tubing section connected to the inlet port, and a second tubing section connected to the outlet port. The fluid injector system further includes a controller programmed or configured to determine a status of the administration line.

In some aspects or examples, the first tubing section includes a first inlet fitting configured for connection to a first fluid reservoir of the fluid injector system and a second inlet fitting configured for connection to a second fluid reservoir of the fluid injector system. The first inlet fitting is configured to connect to the second inlet fitting during storage or shipment of the administration line.

In some aspects or examples, the first tubing section includes an inlet fitting configured for connection to an intermediate tubing set in fluid communication with at least one fluid reservoir of the fluid injector system. The inlet fitting is configured to connect to the body of the fluid verification module during storage or shipment of the administration line.

In some aspects or examples, the body of the fluid verification module further defines a priming port, and the second tubing section includes an outlet fitting configured to connect to the priming port during storage or shipment of the administration line.

In some aspects or examples, the priming port is in fluid communication with a priming cavity, and the priming cavity is configured to receive and hold priming fluid from the outlet fitting during a priming operation of the administration line.

In some aspects or examples, the fluid injector system further includes at least one sheet material disposed within the priming cavity. The at least one sheet material includes a first sheet material having indicia and a second sheet material which transitions from an opaque state to an at least partially translucent state when the second sheet material is contacted by the priming fluid. The indicia on the first sheet material is obstructed by the second sheet material when the second sheet material is in the opaque state. The indicia on the first sheet material is visible via a window in the body when the second sheet material is in the translucent state.

In some aspects or examples the fluid injector system further includes at least one probe for measuring electrical resistance in communication with the controller and at least one sheet material disposed within the priming cavity. The at least one sheet material is configured to change in electrical resistance when contacted by the priming fluid. When the fluid verification module is mounted to the housing of the fluid injector system, the at least one sheet material is configured to interface with the at least one probe such that electrical resistance of the at least one sheet material can be determined by the controller.

In some aspects or examples, the controller is programmed or configured to prohibit performance of an injection procedure in response to determining, via the at least one probe, that the at least one sheet material has been previously contacted by the priming fluid.

In some aspects or examples, the fluid injector system further includes a light source in communication with the controller. At least a portion of the body of the fluid verification module is configured to act as a lens to display light emitted from a light source by the controller.

In some aspects or examples, the fluid injector system further includes an imaging device in communication with the controller. The fluid channel is at least partially transparent such that the controller can determine the presence or absence of fluid in the fluid channel via the imaging device.

In some aspects or examples, the controller is programmed or configured to halt performance of a fluid injection procedure in response to detecting air in the fluid channel via the imaging device.

In some aspects or examples, the fluid injector system further includes a strain gauge in communication with the controller. The fluid channel is flexible and configured to interface with the strain gauge such that the controller can determine fluid pressure in the administration line via the strain gauge.

In some aspects or examples, the fluid injector system further includes at least one of an inlet one-way valve associated with the inlet port and an outlet one-way valve associated with the outlet port. At least one of the inlet one-way valve and the outlet one-way valve prohibit fluid flow in an upstream direction from the second tubing section toward the first tubing section.

Further aspects and examples of the present disclosure are set forth in the following numbered clauses.

Clause 1. An administration line for use with a fluid injector system, the administration line comprising: a fluid verification module configured to be in operative communication with a housing of the fluid injector system such that the fluid injector system can determine a status of the administration line, the fluid verification module comprising: a body defining an inlet port, an outlet port, and a fluid channel extending from the inlet port to the outlet port; a first tubing section connected to the inlet port; and a second tubing section connected to the outlet port.

Clause 2. The administration line of clause 1, wherein the first tubing section comprises: a first inlet fitting configured for connection to a first fluid reservoir of the fluid injector system; and a second inlet fitting configured for connection to a second fluid reservoir of the fluid injector system, wherein the first inlet fitting is configured to connect to the second inlet fitting during storage or shipment of the administration line.

Clause 3. The administration line of clause 1 or 2, wherein the first tubing section comprises: an inlet fitting configured for connection to an intermediate tubing set in fluid communication with at least one fluid reservoir of the fluid injector system, wherein the inlet fitting is configured to connect to the body of the fluid verification module during storage or shipment of the administration line.

Clause 4. The administration line of any of clauses 1 to 3, wherein the body further defines a priming port, and wherein the second tubing section comprises an outlet fitting configured to connect to the priming port during storage or shipment of the administration line.

Clause 5. The administration line of any of clauses 1 to 4, wherein the priming port is in fluid communication with a priming cavity, and wherein the priming cavity is configured to receive and hold priming fluid from the outlet fitting during a priming operation of the administration line.

Clause 6. The administration line of any of clauses 1 to 5, further comprising at least one sheet material disposed within the priming cavity, the at least one sheet material comprising: a first sheet material having indicia; and a second sheet material which transitions from an opaque state to an at least partially translucent state when the second sheet material is contacted by the priming fluid, wherein the indicia on the first sheet material is obstructed by the second sheet material when the second sheet material is in the opaque state, and wherein the indicia on the first sheet material is visible via a window in the body when the second sheet material is in the translucent state.

Clause 7. The administration line of any of clauses 1 to 6, further comprising at least one sheet material disposed within the priming cavity, wherein the at least one sheet material is configured to change in electrical resistance when contacted by the priming fluid, and wherein, when the fluid verification module is mounted to the housing of the fluid injector system, the at least one sheet material is configured to interface with at least one probe of the fluid injector system for measuring electrical resistance of the at least one sheet material.

Clause 8. The administration line of any of clauses 1 to 7, wherein the body of the fluid verification module further comprises a capillary channel in fluid communication with the priming cavity and configured to take up at least a portion of the priming fluid via capillary action.

Clause 9. The administration line of any of clauses 1 to 8, wherein at least a portion of the body of the fluid verification module is configured to act as a lens to display light emitted from a light source of the fluid injector system.

Clause 10. The administration line of any of clauses 1 to 9, wherein the body of the fluid verification module comprises one or more engagement features configured for securing the fluid verification module to the housing of the fluid injector system.

Clause 11. The administration line of any of clauses 1 to 10, wherein the fluid channel is at least partially transparent such that an imaging device of the housing can determine the presence or absence of fluid in the fluid channel.

Clause 12. The administration line of any of clauses 1 to 11, wherein the fluid channel is flexible and configured to interface with a strain gauge of the housing such that the strain gauge can determine fluid pressure in the administration line.

Clause 13. The administration line of any of clauses 1 to 12, further comprising at least one of: an inlet one-way valve associated with the inlet port; and an outlet one-way valve associated with the outlet port, wherein at least one of the inlet one-way valve and the outlet one-way valve prohibit fluid flow in an upstream direction from the second tubing section toward the first tubing section.

Clause 14. A fluid injector system configured to perform an injection procedure in connection with a diagnostic imaging procedure, the fluid injector system comprising: an administration line comprising: a fluid verification module, the fluid verification module comprising a body defining an inlet port, an outlet port, and a fluid channel extending from the inlet port to the outlet port; a first tubing section connected to the inlet port; and a second tubing section connected to the outlet port. a controller programmed or configured to determine a status of the administration line.

Clause 15. The fluid injector system of clause 14, wherein the first tubing section comprises: a first inlet fitting configured for connection to a first fluid reservoir of the fluid injector system; and a second inlet fitting configured for connection to a second fluid reservoir of the fluid injector system, wherein the first inlet fitting is configured to connect to the second inlet fitting during storage or shipment of the administration line.

Clause 16. The fluid injector system of clause 14 or 15, wherein the first tubing section comprises: an inlet fitting configured for connection to an intermediate tubing set in fluid communication with at least one fluid reservoir of the fluid injector system, wherein the inlet fitting is configured to connect to the body of the fluid verification module during storage or shipment of the administration line.

Clause 17. The fluid injector system of any of clauses 14 to 16, wherein the body of the fluid verification module further defines a priming port, and wherein the second tubing section comprises an outlet fitting configured to connect to the priming port during storage or shipment of the administration line.

Clause 18. The fluid injector system of any of clauses 14 to 17, wherein the priming port is in fluid communication with a priming cavity, and wherein the priming cavity is configured to receive and hold priming fluid from the outlet fitting during a priming operation of the administration line.

Clause 19. The fluid injector system of any of clauses 14 to 18, further comprising at least one sheet material disposed within the priming cavity, the at least one sheet material comprising: a first sheet material having indicia; and a second sheet material which transitions from an opaque state to an at least partially translucent state when the second sheet material is contacted by the priming fluid, wherein the indicia on the first sheet material is obstructed by the second sheet material when the second sheet material is in the opaque state, and wherein the indicia on the first sheet material is visible via a window in the body when the second sheet material is in the translucent state.

Clause 20. The fluid injector system of any of clauses 14 to 19, further comprising: at least one probe for measuring electrical resistance in communication with the controller; and at least one sheet material disposed within the priming cavity, wherein the at least one sheet material is configured to change in electrical resistance when contacted by the priming fluid, and wherein, when the fluid verification module is mounted to the housing of the fluid injector system, the at least one sheet material is configured to interface with the at least one probe such that electrical resistance of the at least one sheet material can be determined by the controller.

Clause 21. The fluid injector system of any of clauses 14 to 20, wherein the controller is programmed or configured to prohibit performance of an injection procedure in response to determining, via the at least one probe, that the at least one sheet material has been previously contacted by the priming fluid.

Clause 22. The fluid injector system of any of clauses 14 to 21, further comprising a light source in communication with the controller, wherein at least a portion of the body of the fluid verification module is configured to act as a lens to display light emitted from a light source by the controller.

Clause 23. The fluid injector system of any of clauses 14 to 22, further comprising an imaging device in communication with the controller, wherein the fluid channel is at least partially transparent such that the controller can determine the presence or absence of fluid in the fluid channel via the imaging device.

Clause 24. The fluid injector system of any of clauses 14 to 23, wherein the controller is programmed or configured to halt performance of a fluid injection procedure in response to detecting air in the fluid channel via the imaging device.

Clause 25. The fluid injector system of any of clauses 14 to 24, further comprising a strain gauge in communication with the controller, wherein the fluid channel is flexible and configured to interface with the strain gauge such that the controller can determine fluid pressure in the administration line via the strain gauge.

Clause 26. The fluid injector system of any of clauses 14 to 25, further comprising at least one of: an inlet one-way valve associated with the inlet port; and an outlet one-way valve associated with the outlet port, wherein at least one of the inlet one-way valve and the outlet one-way valve prohibit fluid flow in an upstream direction from the second tubing section toward the first tubing section.

These and other features and characteristics of administration lines, fluid injector systems, and methods of operation and functions of the related elements of structures and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only.

DETAILED DESCRIPTION

Figure 1:
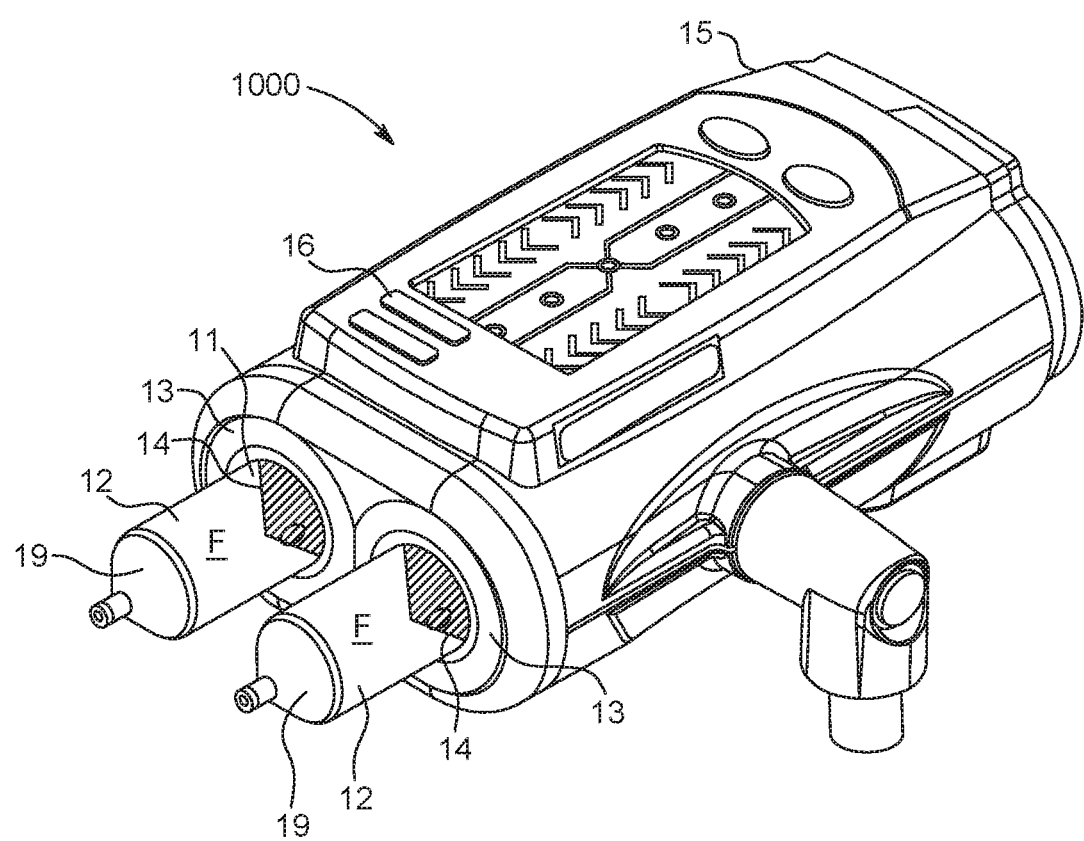
FIG. 1 is a perspective view of a fluid injector system in accordance with an aspect or example of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe of a multi-patient disposable set, the term "proximal" refers to a portion of a syringe nearest a piston for delivering fluid from a syringe.

Spatial or directional terms, such as "left", "right", "inner", "outer", "above", "below", and the like, are not to be considered as limiting as the disclosure can assume various alternative orientations.

All numbers used in the specification and claims are to be understood as being modified in all instances by the term "about". The terms "approximately", "about", and "substantially" mean a range of plus or minus ten percent of the stated value.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

It is also to be understood that the specific devices and processes illustrated in the attached drawings, and described in the following specification, are simply exemplary examples of the disclosure. Hence, specific dimensions and other physical characteristics related to the examples disclosed herein are not to be considered as limiting.

When used in relation to a component of a fluid injector system such as a fluid reservoir, a syringe, or a fluid line, the term "distal" refers to a portion of said component nearest to a patient. When used in relation to a component of a fluid injector system such as a fluid reservoir, a syringe, or a fluid line, the term "proximal" refers to a portion of said component nearest to the injector of the fluid injector system (i.e. the portion of said component farthest from the patient). When used in relation to a component of a fluid injector system such as a fluid reservoir, a syringe, or a fluid line, the term "upstream" refers to a direction away from the patient and towards the injector of the fluid injector system. For example, if a first component is referred to as being "upstream" of a second component, the first component is located nearer to the injector than the second component is to the injector. When used in relation to a component of a fluid injector system such as a fluid reservoir, a syringe, or a fluid line, the term "downstream" refers to a direction towards the patient and away from the injector of the fluid injector system. For example, if a first component is referred to as being "downstream" of a second component, the first component is located nearer to the patient than the second component is to the patient.

Although the present disclosure is described primarily in the context of the MEDRAD® Stellant CT Injection System, it will be apparent to persons of ordinary skill in the art that the present disclosure can be applied to a variety of injection systems inclusive of their associated disposables (e.g., syringes, tubing, etc.). Examples of such injection systems include the MEDRAD® Salient CT Injection System, MEDRAD® Stellant FLEX CT Injection System, the MEDRAD® Centargo CT Injection System, the MEDRAD® MRXperion MR Injection System and the MEDRAD® Mark 7 Arterion Injection System offered by Bayer HealthCare LLC.

Referring to the drawings in which like reference characters refer to like parts throughout the several views thereof, the present disclosure is generally directed to fluid injector systems, administration lines, and methods of operation thereof.

Referring first to FIG. 1, an example of a fluid injector system 1000 in accordance with the present disclosure includes a housing 15 and at least one fluid reservoir, such as at least one syringe 12. The fluid injector system 1000 further includes a piston 13 associated with each of the syringes 12 that drives a plunger 14 within a barrel of the syringe 12. The at least one syringe 12 is generally adapted to releasably interface with the housing 15 at a syringe port. The at least one syringe 12 may be oriented in any manner such as upright, downright, or positioned at any degree angle. The fluid injector system 1000 is generally configured to deliver at least one medical fluid F to a patient during an injection procedure. The fluid injector system 1000 is configured to releasably receive the at least one syringe 12, which is to be filled with at least one medical fluid F, such as an imaging contrast media, saline solution, or any desired medical fluid. Each syringe 12 may be filled with a different medical fluid F. The fluid injector system 1000 may be a multi-syringe injector, as shown, wherein several syringes 12 may be oriented side-by-side or in another spatial relationship and are separately actuated by respective pistons associated with the injector system 1000.

With continued reference to FIG. 1, the fluid injector system 1000 may be used during a medical procedure to inject the at least one medical fluid F into the vasculature of a patient by driving the plungers 14 associated with the at least one syringe 12 with the at least one piston 13. The at least one piston 13 may be reciprocally operable upon the plunger 14. Upon engagement, the at least one piston 13 may move the plunger 14 toward a proximal end of the at least one syringe 12 to draw the medical fluid F into the at least one syringe 12 from a bulk fluid reservoir (not shown), such as a vial, bottle, or intravenous bag. The at least one piston 13 may further move the plunger 14 toward a distal end 19 of the at least one syringe 12 to expel the fluid F from the at least one syringe 12 out a patient line and to a patient at a vascular access site.

The housing 15 of the fluid injector system 1000 may contain components of an electronic control device 900 (see FIGS. 2, 3, 6 to 8, and 15), e.g. a controller such as at least one processor programmed or configured to receive, store, and execute instructions for actuating the fluid injector system 1000. The controller 900 may, for example, be programmed or configured to execute one or more injection procedures and/or one or more priming procedures.

Further details and examples of suitable non-limiting powered injector systems, including syringes, controllers, air detectors, and fluid path sets are described in U.S. Pat. Nos. 5,383,858; 7,553,294; 7,666,169; 8,945,051; 10,022,493; and 10,507,319, the disclosures of which are hereby incorporated by reference in their entireties.

Figure 2:
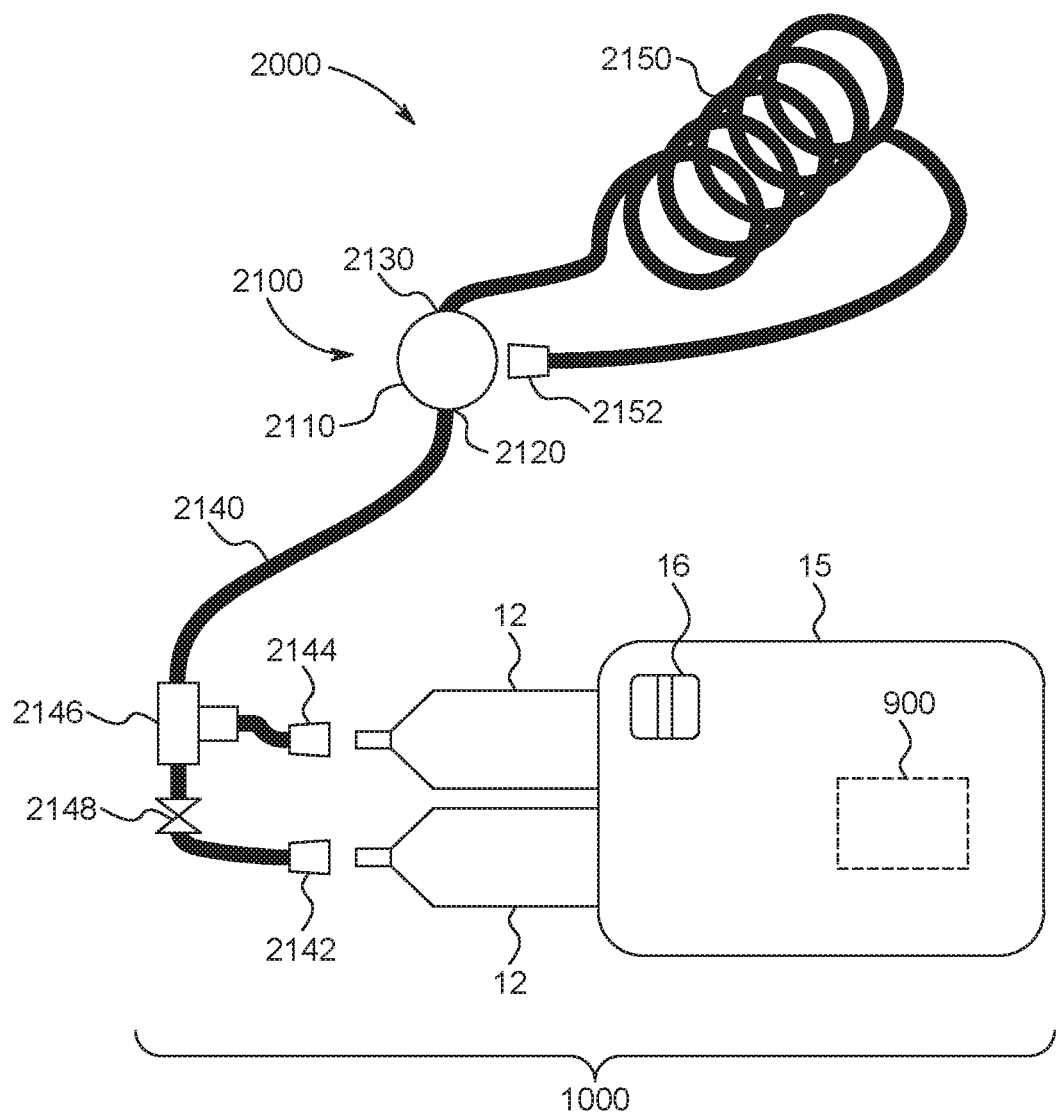
FIG. 2 is a top view of the fluid injector system of FIG. 1 including a patient administration line in accordance with an aspect or example of the present disclosure.
Figure 3:
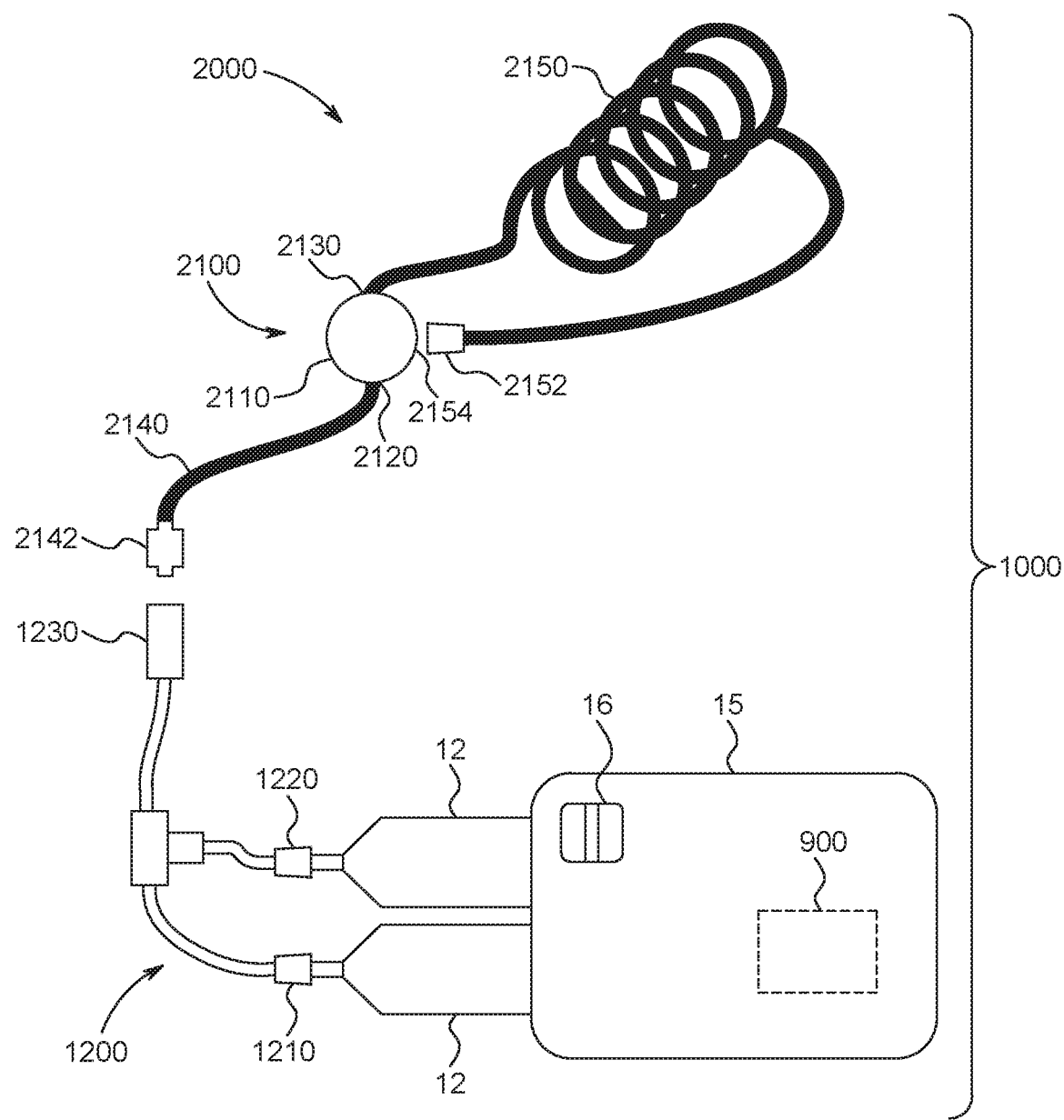
FIG. 3 is a top view of the fluid injector system of FIG. 1 including a patient administration line in accordance with another aspect or example of the present disclosure.

FIGS. 2 and 3 show the fluid injector system 1000 including a patient administration line assembly 2000 (hereinafter "administration line 2000") in accordance with various aspects and examples of the present disclosure. The administration line 2000 includes a fluid verification module 2100 that may perform a variety of functions that will be discussed in greater detail herein, but which generally relate to priming the administration line 2000, enforcing replacement of the administration line 2000 at recommended intervals, displaying alerts to a user, and other functions. Furthermore, the fluid verification module 2100 may include features to prevent contamination of upstream components, such as one or more integral check valves (see FIG. 10). The fluid verification module 2100 includes a body 2110, which may be an at least partially hollow structure defining various ports, channels, chambers and the like as will be described in detail herein. As shown in the accompanying drawings, the body 2110 may be cylindrical in shape, though any suitable shape may be used.

An inlet port 2120 and an outlet port 2130 may be defined in the body 2110 of the fluid verification module 2100. The inlet port 2120 is configured to receive a first tubing section 2140 which extends proximally toward the at least one syringe 12. The outlet port 2130 is configured to receive a second tubing section 2150 that extends distally for ultimately connecting to a needle or catheter (not shown) inserted into a patient. The first tubing section 2140 and the second tubing section 2150 may be permanently and irreversibly attached to the body 2110 of the fluid verification module 2100, such as via a solvent weldment, to prevent reuse of the first tubing section 2140 and the second tubing section 2150 with a different fluid verification module 2100. However, it is within the scope of the present disclosure that the first tubing section 2120 and the second tubing section 2150 may be removably attached to the body 2110, such as via a barb fitting, luer connector, bayonet connector, or the like. In some aspects or examples, the inlet port 2120, or a portion of the first tubing section 2140 adjacent the inlet port 2120, may include a one-way valve, e.g. a check valve, to prevent fluid flow toward the inlet port 2120. Similarly, the outlet port 2130, or a portion of the second tubing section 2150 adjacent the outlet port 2130, may include a one-way valve, e.g. a check valve, to prevent fluid flow toward the inlet port 2120. As will be described herein in connection with FIG. 10, the one-way valves may also be integral to the inlet port 2120 and the outlet port 2130.

Referring specifically to the aspect or example of the administration line 2000 shown in FIG. 2, the first tubing section 2140 includes a first inlet fitting 2142 and a second inlet fitting 2144, each of which is configured to connect, either directly or indirectly, to one of the at least one syringes 12. The first tubing section 2140 includes a Y- or T-fitting 2146 that branches the first tubing section 2140 into two fluid paths respectively extending to the first inlet fitting 2142 and the second inlet fitting 2144. The first tubing section 2140 may further include a one-way valve 2148, e.g. a check valve, between the Y- or T-fitting 2146 and the first inlet fitting 2142 to prevent backflow of fluid into the syringe 12 to which the first inlet fitting 2142 is connected. In particular, the one-way valve 2148 prevents contrast under high injection pressure from backflowing into the syringe 12 containing saline. The second tubing section 2150 includes an outlet fitting 2152 configured to connect, either directly or indirectly, to a needle or catheter (not shown) inserted into a patient. Each of the first inlet fitting 2142, the second inlet fitting 2144, and the outlet fitting 2152 may be a luer connector, hose barb, bayonet connector, or any other type of connector for establishing fluid communication between components. The aspect or example of the fluid administration line 2000 shown in FIG. 2 may be used as a single-use line, which must be replaced in full after the fluid injector system 1000 performs an injection procedure. Replacement of the administration line 2000 after an injection procedure may be enforced by the controller 900, as described herein in connection with FIG. 14.

Figure 4:
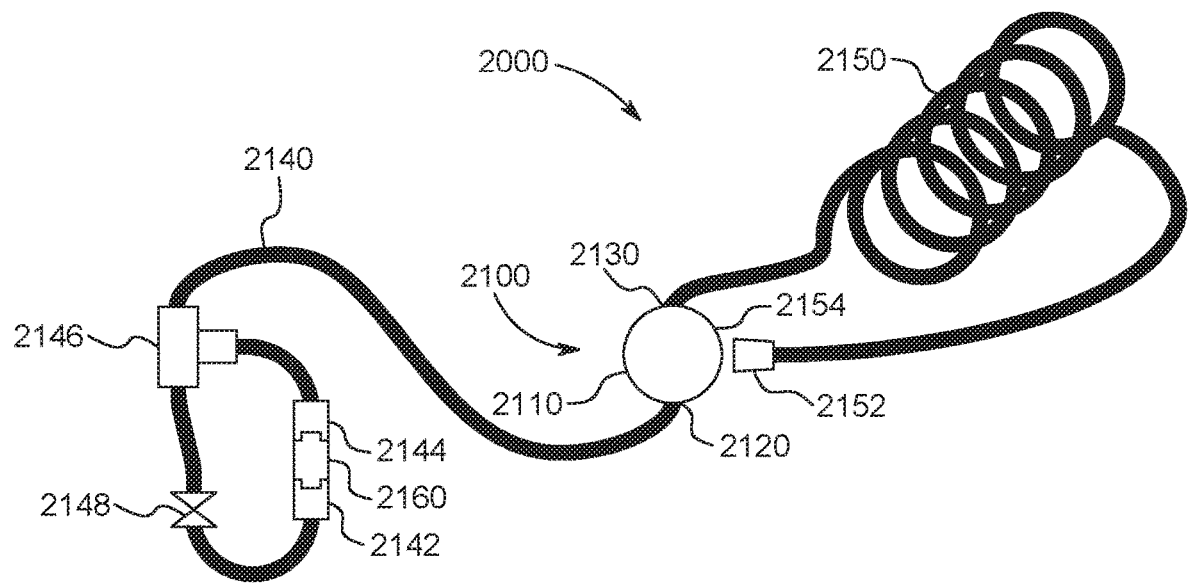
FIG. 4 is a top view of the patient administration line of FIG. 2, shown in a storage or shipment position.

Referring now to FIG. 4, the aspect or example of the administration line 2000 shown in FIG. 2 is illustrated in a state for shipment or storage. To prevent contaminants from entering the administration line 2000 before use, the first inlet fitting 2142, the second inlet fitting 2144, and the outlet fitting 2152 may be covered to prevent exposure to the ambient environment. In some aspects or examples, one or more of the first inlet fitting 2142, the second inlet fitting 2144, and the outlet fitting 2152 may be fitted with a dust cap. In some aspects or examples, one or more of the first inlet fitting 2142, the second inlet fitting 2144, and the outlet fitting 2152 may be fitted into a port in the body 2110. For example, as shown in FIG. 4, each of the first inlet fitting 2142 and the second inlet fitting 2144 may be mated to a common dust cap 2160, and the outer fitting 2152 is fitted into a priming port 2154 in the body 2110 of the fluid verification module 2100. With this arrangement, only a single disposable, namely the dust cap 2160, is required to seal in the administration line 2000 from contaminants from the ambient environment. Other arrangements are also understood to be within the scope of the present disclosure. For example, the outlet fitting 2152 could be fitted into the dust cap 2160 or into a separate dust cap. Alternatively, the first inlet fitting 2142 and the second inlet fitting 2144 may be fitted into ports in the fluid verification module 2100.

With continued reference to FIG. 4, the administration line 2000 may be prepared for use in an injection procedure by removing the dust cap 2160 from the first inlet fitting 2142 and the second inlet fitting 2144. The first inlet fitting 2142 and the second inlet fitting 2144 may then be respectively connected to the one or more syringes 12, as shown in FIG. 2. Subsequent to a priming operation, the outlet fitting 2152 may be removed from the priming port 2154 of the fluid verification module 2100 and connected to a catheter, needle, or the like (not shown) for insertion into the patient.

Now referring specifically to the aspect or example of the administration line 2000 shown in FIG. 3, the first tubing section 2140 includes an inlet fitting 2142 configured to connect to an intermediate tubing set 1200, and the second tubing section 2150 includes an outlet fitting 2152 configured to connect to a needle or catheter (not shown) inserted into a patient. The intermediate tubing set 1200 may in turn be connected to the at least one syringe 12. In particular, the intermediate tubing set 1200 may include a first inlet fitting 1210 configured for connection to a first of the syringes 12, a second inlet fitting 1220 configured for connection to a second of the syringes 12, and an outlet fitting 1230 configured for connection to the first tubing section 2140 of the administration line 2000. In some aspects and examples, the intermediate tubing set 1200 may include one or more one-way valves (e.g. check valves, not shown in FIG. 3) located and oriented to prevent backflow of fluid into various components of the fluid injector system 1000 or associated with the fluid injector system 1000, such as the one or more syringes 12.

Each of the inlet fitting 2142 and the outlet fitting 2152 of the administration line 2000 may be a luer connector, hose barb, bayonet connector, or any other type of connector for establishing fluid communication between components. The inlet fitting 2142 may, in particular, be a multi-guard connector which includes a recessed port to prevent accidental touch contamination when a connection is made between the administration line 2000 and the intermediate tubing set 1200. Similarly, each of the first inlet fitting 1210 and the second inlet fitting 1220 of the intermediate tubing set 1200 may be a luer connector, hose barb, bayonet connector, or any other type of connector for establishing fluid communication between components. The outlet fitting 1230 may be a multi-guard connector which prevents accidental touch contamination between the administration line 2000 and the intermediate tubing set 1200.

The aspect or example of the fluid administration line 2000 shown in FIG. 3 may be used with a multi-patient intermediate tubing set 1200. That is, the intermediate tubing set 1200 may be used for multiple injection protocols and/or patients, for example a predetermined number of injection procedures and/or patients, performed by the fluid injector system 1000. The administration line 2000 may be replaced after each injection procedure, but the backflow prevention features of the administration line 2000 allow for reuse of the multi-patient intermediate tubing set 1200 without a risk of cross contamination. Replacement of the administration line 2000 after an injection procedure may be enforced by the controller 900, as described herein in connection with FIG. 14.

Figure 5:
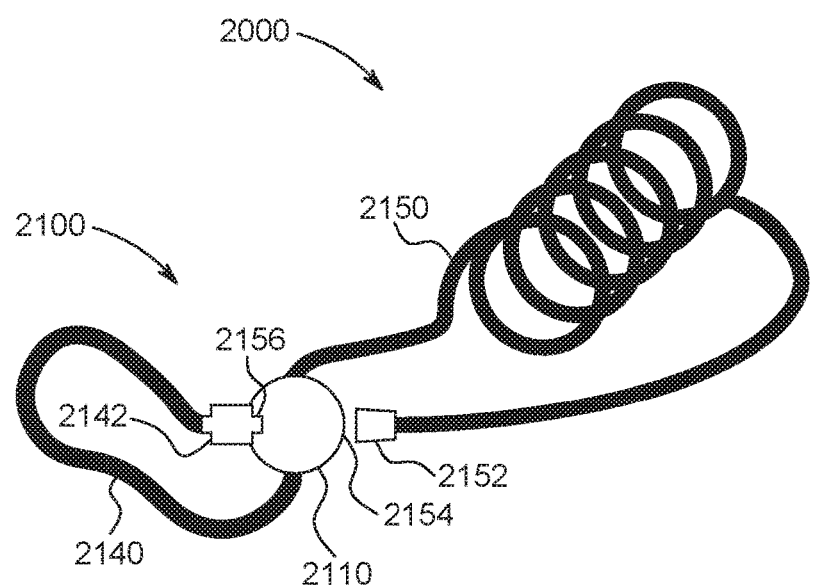
FIG. 5 is a top view of the patient administration line of FIG. 3, shown in a storage or shipment position.

Referring now to FIG. 5, the aspect or example of the administration line 2000 shown in FIG. 3 is illustrated in a state for shipment or storage. To prevent contaminants from entering the administration line 2000, the inlet fitting 2142 and the outlet fitting 2152 may be covered to prevent exposure to the ambient environment. In some aspects or examples, the inlet fitting 2142 may fit into a blind port 2156 and the outlet fitting 2152 may be fitted into a priming port 2154 in the body 2110. In other aspects or examples, one or both of the inlet fitting 2142 and the outlet fitting 2152 may be fitted with individual dust caps or with a common dust cap, similar to the manner in which the first and second inlet fittings 2142, 2144 are fitted to the dust cap 2160 in the aspect or example shown in FIG. 4. The administration line 2000 may be prepared for use in an injection procedure by removing the inlet fitting 2142 from the blind port 2156. The first inlet fitting 2142 may then be connected to the one or more syringes 12 via the multi-patient intermediate tubing set 1200, as shown in FIG. 3. Upon completion of a priming operation, the outlet fitting 2152 may be removed from the priming port 2154 of the fluid verification module 2100 and connected to a catheter, needle, or the like (not shown) for insertion into a vascular access site of the patient.

Figure 6:
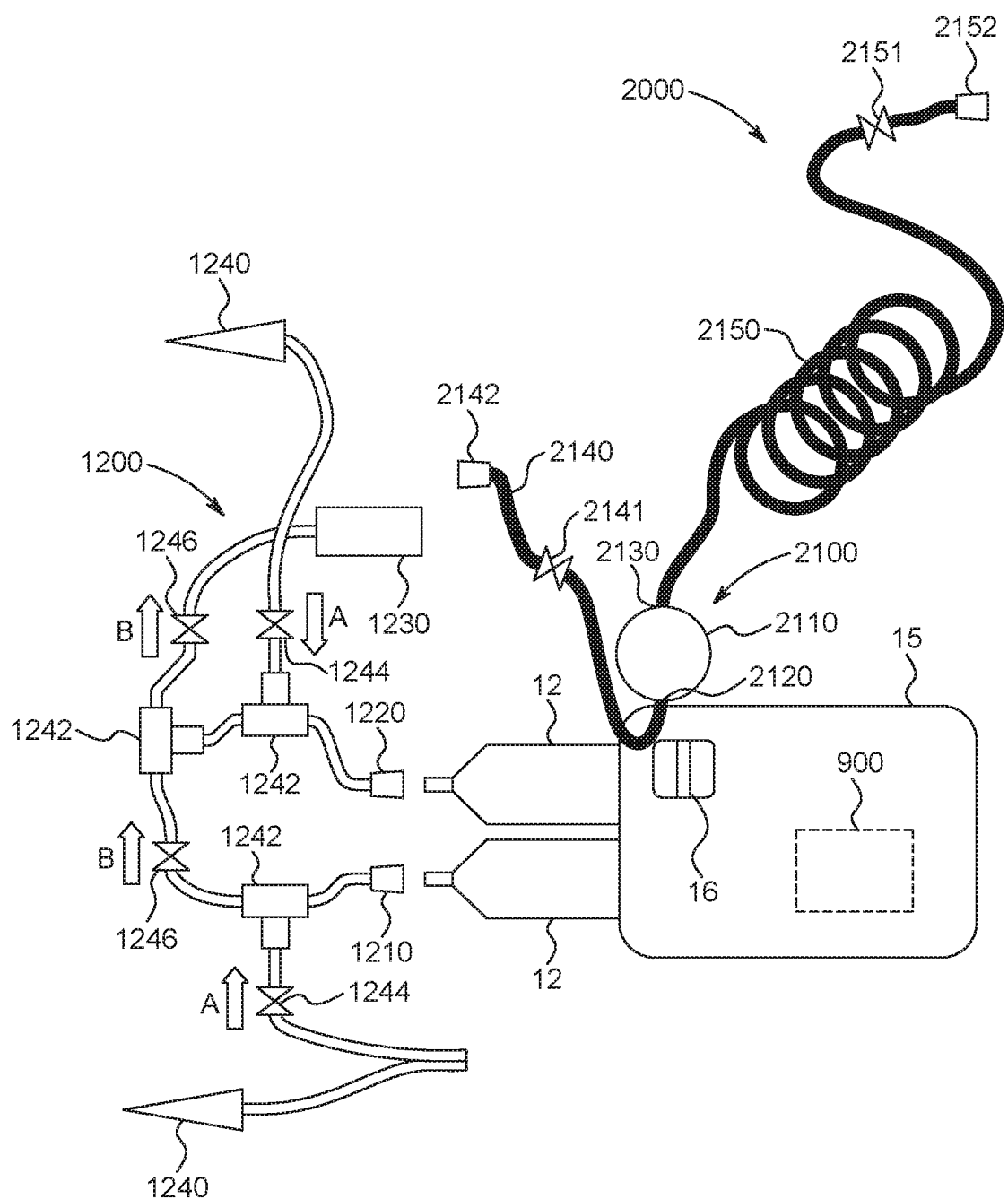
FIG. 6 is a top view of the fluid injector system of FIG. 1 including a patient administration line in accordance with another aspect or example of the present disclosure.

Referring now to FIG. 6, another aspect or example of the fluid injector system 1000 is shown. The aspect or example shown in FIG. 6 is similar to that shown in FIG. 3, with an expanded intermediate tubing set 1200. To the extent that specific components of the aspect shown in FIG. 6 are not described in detail, it is to be understood that such components are the same or similar to like components of the aspect shown in FIG. 3. In the aspect or example shown in FIG. 6, the intermediate tubing set 1200 includes one or more fluid connectors 1240, such as bottle spikes, configured to fluidly communicate with a fluid reservoir (not shown) such as a bottle, vial, container, bag, pouch, or the like. The intermediate tubing set 1200 may further include one or more Y- or T-fittings 1242 and one or one-way valves 1244, 1246, e.g. check valves, to define the flow path and flow direction between the first inlet fitting 1210, the second inlet fitting 1220, the outlet fitting 1230, and the fluid connectors 1240.

With continued reference to FIG. 6, in some aspects or examples, the administration line 2000 may include an inlet one-way valve 2141, such as a check valve, in the first tubing section 2140 to prevent fluid flow toward the inlet fitting 2142. Similarly, the administration line 2000 may include an outlet one-way valve 2151, such as a check valve, in the second tubing section 2150 to prevent fluid flow toward the inlet fitting 2142. The inlet one-way valve 2141 and the outlet one-way valve 2151 may be used alternatively or in addition to the one-way valves formed in the inlet port 2120 and the outlet port 2130, as described in connection with FIGS. 2 and 3.

Figure 7:
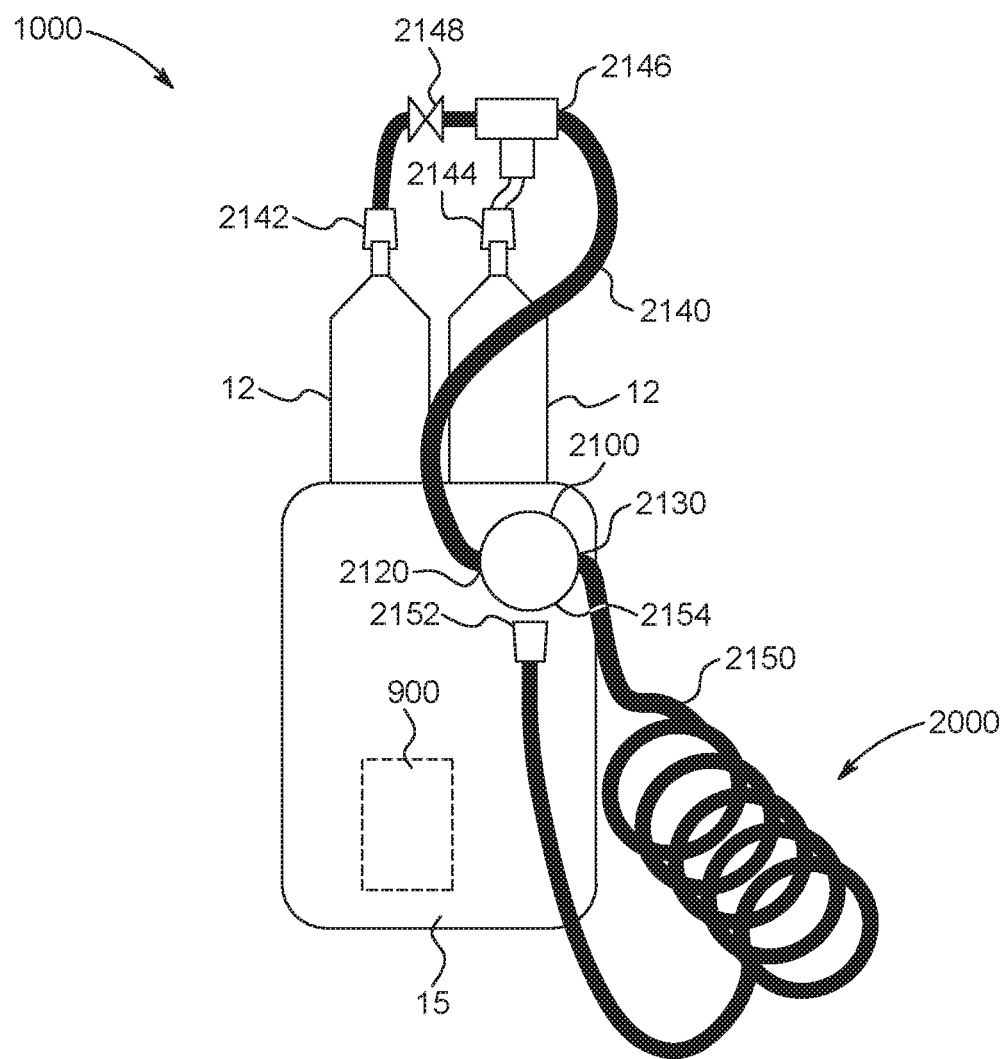
FIG. 7 is a top view of the fluid injector system of FIG. 2, with the administration line mounted to the housing of the fluid injector.
Figure 8:
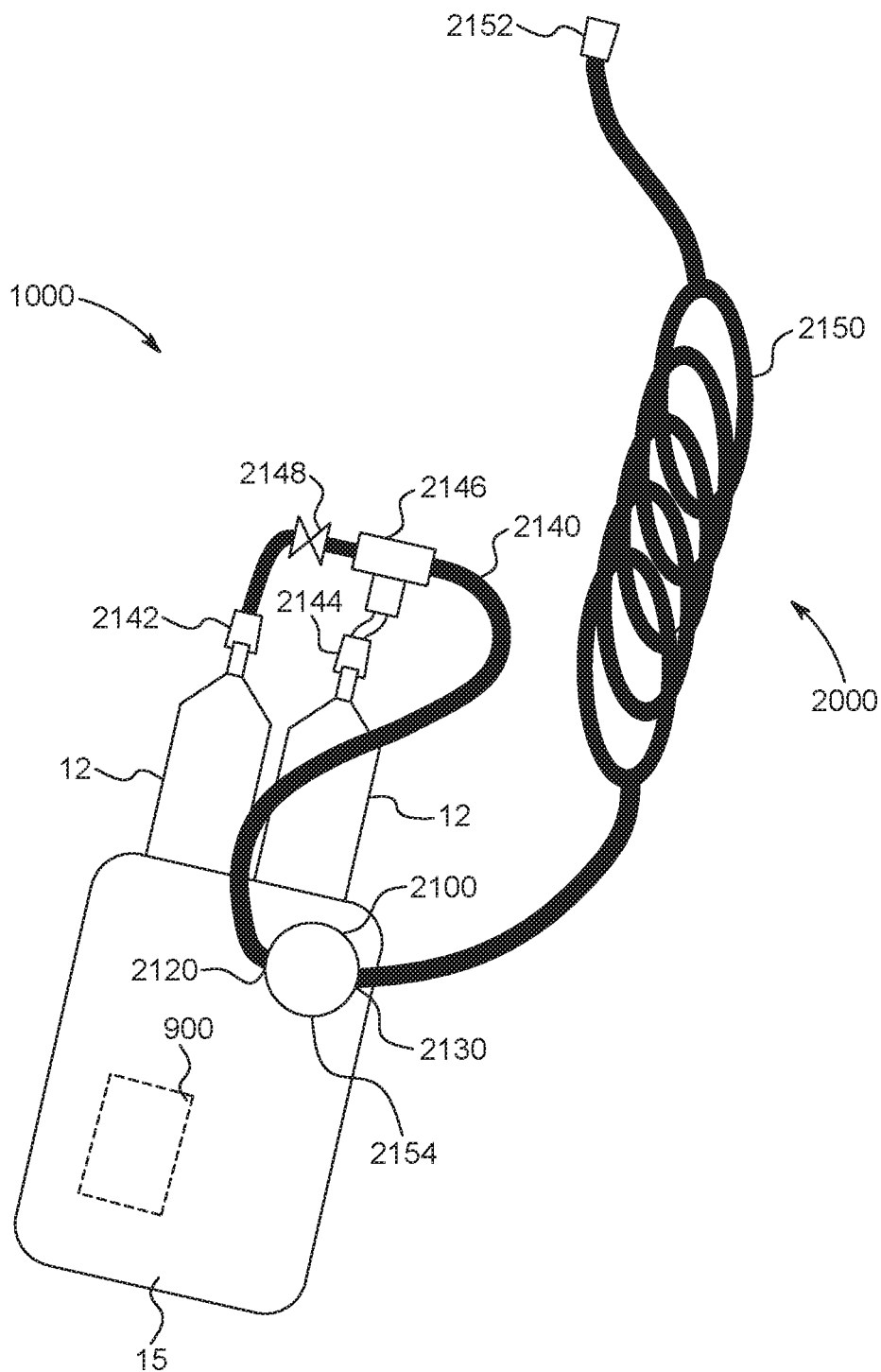
FIG. 8 is a top view of the fluid injector system of FIG. 2, with the administration line in position for connection to a patient.

Referring again to FIGS. 1-3, the housing 15 of the fluid injector system 1000 may include a mounting flange and control interface structure 16 (hereinafter "mounting flange 16") for holding the fluid verification module 2100. The mounting flange 16 allows the housing 15 of the fluid injector system 1000 to be in operative communication with the fluid verification module 2100 such that the housing 15 may interact with the fluid verification module 2100 to determine a status of the administration line 2000. FIGS. 7 and 8 show the fluid injector system 1000 of FIG. 2 with the fluid verification module 2100 attached to the mounting flange 16, and with the first inlet fitting 2142 and the second inlet fitting 2144 respectively connected to the syringes 12. In FIG. 7, the outlet fitting 2152 is attached to the priming port 2154 of the fluid verification module 2100, such that administration line 2000 is ready to be primed or in the process of being primed. In FIG. 8, the outlet fitting 2152 is detached from the priming port 2154 of the fluid verification module 2100, such that the administration line 2000 is ready for connection to a needle, catheter, or the like (not shown) and ultimately to a vascular access site of the patient.

Figure 9:
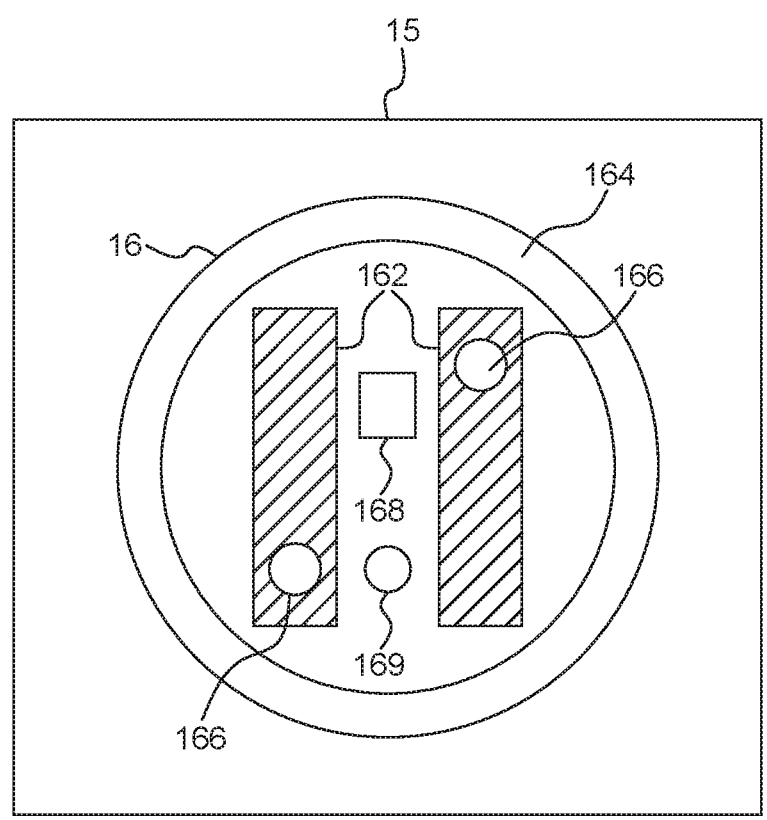
FIG. 9 is a detail view of a mounting flange of the fluid injector system of FIG. 1.

Referring now to FIG. 9, the mounting flange 16 may include one or more engagement features 162 on the housing 15 of the fluid injector system 1000 that are configured to interface with the body 2110 of the fluid verification module 2100. The one or more engagement features 162 may include tabs, grooves, internal or external threads, channels, or other features that interface with corresponding engagement features 2113 (see FIG. 11) on the body 2110 of the fluid verification module 2100. The one or more engagement features 162 may include sensors or the like to verify that the corresponding engagement features 2113 of the fluid verification module 2100 are connected to the mounting flange 16. The controller 900 may prohibit performance of an injection procedure if the controller 900 determines, based on the sensors in the one or more engagement features 162, that the fluid verification module 2100 is not properly connected to the housing 15, that the administration line 2000 has been previously used for an injection procedure, or if the administration line 2000 has not properly been primed.

The mounting flange 16 may further include one or more sensors, lights, and/or communication devices for interfacing with the fluid verification module 2100. In the aspect or example shown in FIG. 9, the mounting flange 16 includes a light source 164 in the form of an LED ring, two probes 166 for measuring electrical characteristics, a strain gauge 168, and at least one imaging device 169.

The light source 164 may be directed through the body 2110 of the fluid verification module 2100 such that at least of portion of the body 2110 acts as a lens to display light emitted from the light source 164 to the user. The light source 164 may be controlled by the controller 900, which may be programmed or configured to illuminate the light source 164 in distinct colors, patterns, flashes, blinks and/or the like to convey various messages and/or operating statuses to the user. For example, the controller 900 may illuminate the light source 164 in a first color to prompt the user to connect the fluid verification module 2100 to the housing 15; in a second color to indicate that air is present in the administration line 2000; a third color to indicate that the administration line 2000 is primed with saline; a fourth color to indicate medical fluid is flowing through the administration line 2000; and a fifth color to indicate that the administration line 2000 has been used in a prior injection procedure and must be replaced. Details as to how the controller 900 determines the various operating statuses are explained herein in connection with FIG. 14.

The probes 166 may be configured to engage one or more components of the fluid verification module 2100. When the fluid verification module 2100 is not connected to the mounting flange 16, the probes 166 may form an open electrical circuit. When the fluid verification module 2100 is connected to the mounting flange 16, one or more components of the fluid verification module 2100 may close the electrical circuit between the probes 166. The probes 166 may then be used to measure voltage, resistance, or other electrical characteristics of the fluid verification module 2100. For example, the probes 166 may be in communication with the controller 900 and may be configured to measure or detect a change in resistance of a component of the fluid verification module 2100, indicating that the administration line 2000 has been primed. Further details of the interaction between the probes and the fluid verification module 2100 are discussed herein in connection with FIGS. 10-13.

The strain gauge 168 may be configured to be in contact with an interface to a fluid channel, e.g. the main fluid channel 2124 (see FIG. 10), of the fluid verification module 2100. The strain gauge 168 may be in communication with the controller 900 and may be used to measure the deformation of the fluid channel due to fluid pressure and thereby provide the injection pressure value.

The at least one imaging device 169 may be configured to detect and/or determine the presence or absence of fluid within the fluid channel 2124 in the fluid verification module 2100, the type of fluid in the fluid verification module 2100, and/or flow characteristics of fluid within the fluid verification module 2100. The imaging device 169 may include, for example, an optical camera, an infrared camera, an ultrasonic sensor, a barcode reader, an RFID reader, or the like, including combinations thereof. The imaging device 169 may be in communication with the controller 900 such that the controller 900 may execute instructions based on information obtained from the imaging device 169.

Figure 10:
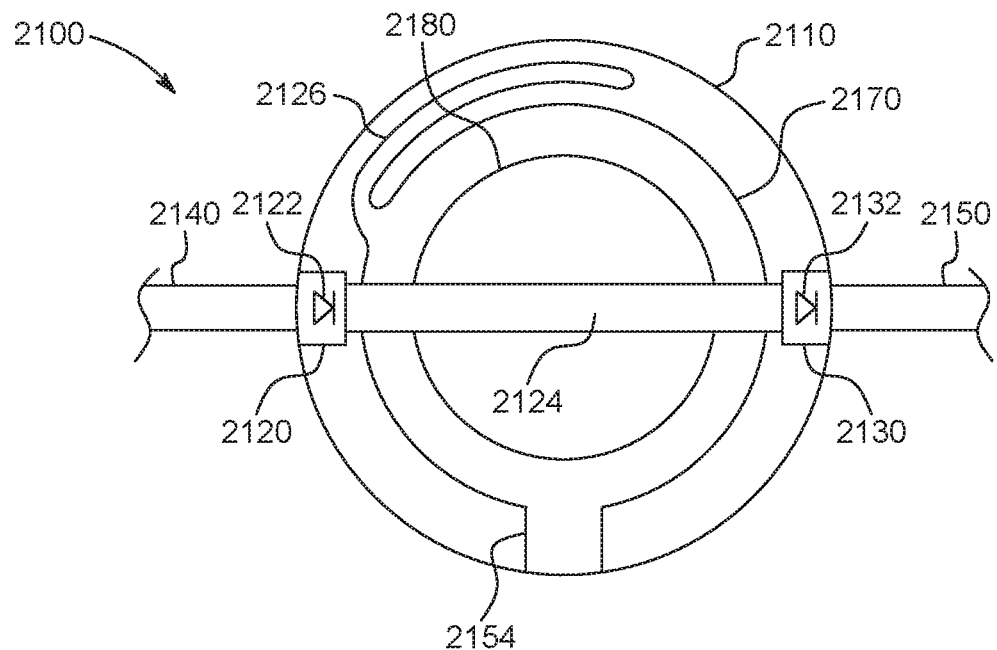
FIG. 10 is a schematic diagram of an inside of a fluid verification module of the administration line in accordance with an aspect or example of the present disclosure.

Referring now to FIG. 10, the body 2110 of the fluid verification module 2100 may house a main fluid channel 2124 extending from the inlet port 2120 to the outlet port 2130. In some aspects or examples, the inlet port 2120 may include a one-way valve 2122, e.g. a check valve, to prevent fluid flow from the main fluid channel 2124 into the first tubing section 2140. Similarly, the outlet port 2130 may include a one-way valve 2132, e.g. a check valve, to prevent fluid flow into the main fluid channel 2124 from the second tubing section 2150. In some aspects or examples, the main fluid channel 2124 may be at least partially formed from a flexible material. As such, the strain gauge 168 of the mounting flange 16 may be utilized to measure fluid pressure within the main fluid channel 2124 based on deformation of the main fluid channel 2124 due to that fluid pressure. In some aspects or examples, the main fluid channel 2124 may be at least partially transparent to allow imaging of fluid within the main fluid channel 2124 by the imaging device 169. The main fluid channel 2124 may not need to be transparent if the imaging device 169 is, for example, an ultrasonic device.

With continued reference to FIG. 10, the priming port 2154 may be in fluid communication with a priming cavity 2170 which may hold a fluid (e.g. saline) used to prime the administration line 2000. In particular, the controller 900 may be programmed or configured to execute a priming operation prior to the outlet fitting 2152 being disconnected from the priming port 2154, such that fluid used for priming the administration line 2000 is contained within the priming cavity 2170. The priming cavity 2170 thus prevent spillage of material and eliminates the need for a priming the administration line 2000 over a waste receptacle. In some aspects or examples, the priming cavity 2170 may be in fluid communication with a capillary channel 2126 which takes up fluid by capillary action, for example during a priming operation of the administration line 2000. The capillary channel 2126 may have any suitable shape to facilitate capillary action, such as an arc as shown in FIG. 10, a spiral, or other shapes. Additional details of the priming operation are described herein in connection with FIG. 14.

Figure 11:
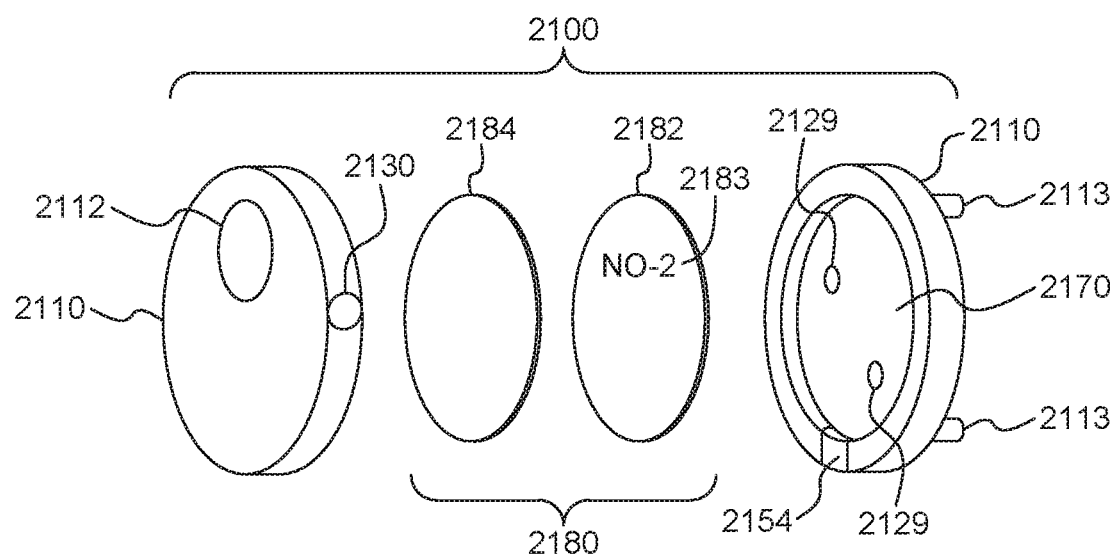
FIG. 11 is an exploded view of a fluid verification module of the administration line in accordance with an aspect or example of the present disclosure.
Figure 12:
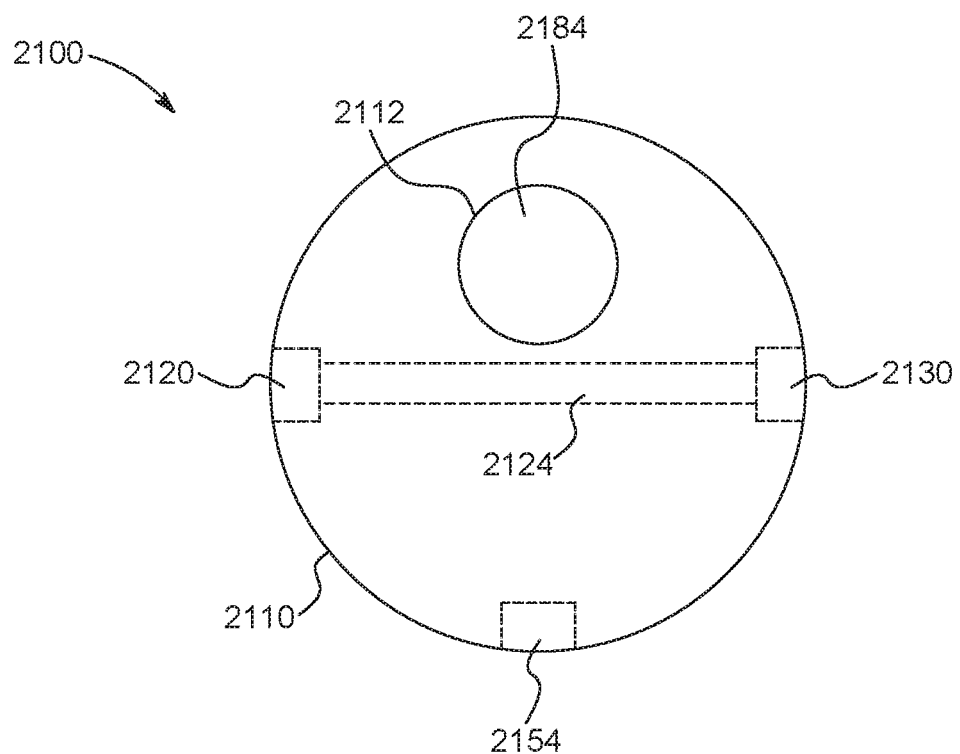
FIG. 12 is a front view of the fluid verification module of FIG. 11, shown prior to priming.
Figure 13:
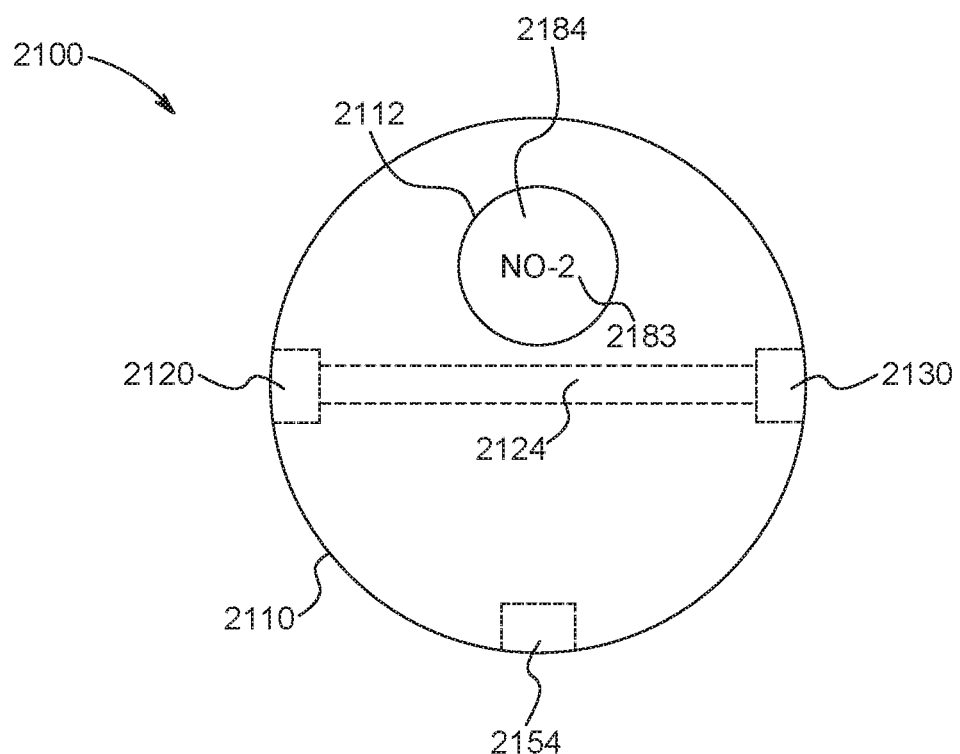
FIG. 13 is a front view of the fluid verification module of FIG. 11, shown after priming.

With continued reference to FIG. 10 and further reference to FIGS. 11-13, in some aspects or examples, the fluid verification module 2100 may include the at least one fluid detection feature for determining and/or indicating whether the administration line 2000 has been used in a previous injection procedure. In some aspects or examples, the at least one fluid detection feature may include at least one sheet material 2180 disposed within the priming cavity 2170. The at least one sheet material 2180 may be absorbent, such that priming fluid in the priming cavity 2170 is at least partially absorbed by the at least one sheet material 2180. The at least one sheet material 2180 may have at least one material property (e.g. electrical resistance) that changes when the at least one sheet material 2180 absorbs medical fluid. In some aspects or examples, the at least one sheet material 2180 may be paper or another thin, absorbent material.

In some aspects or examples, the at least one sheet material 2180 may engage the probes 166 of the mounting flange 16 when the fluid verification module 2100 is connected to the housing 15. The body 2110 of the fluid verification module 2100 may define one or more apertures 2129 through which the probes 166 may extend so as to contact the at least one sheet material 2180. As such, when the fluid verification module 2100 is connected to the housing 15, the at least one sheet material 2180 closes an electrical circuit between the probes 166. The controller 900 may be configured to measure electrical resistance between the probes 166, and, based on the measured electrical resistance, determine whether the at least one sheet material 2180 has absorbed fluid. In this manner, the controller 900 may determine whether fluid is present in the priming cavity 2170, indicating that the administration line 2000 has been previously primed. If the controller 900 determines that the administration line 2000 has been previously primed, and thus has been used in a previous injection procedure (i.e., the administration line 2000 has not been replaced in accordance with predetermined hygienic practices), the controller 900 may prohibit performance of a subsequent injection procedure.

Referring now to FIGS. 11-13, in some aspects or examples, the at least one sheet material 2180 may include a first sheet material 2182 having visual indicia 2183 and a second sheet material 2184 configured to transition from an opaque state to an at partially translucent state when the second sheet material 2184 is contacted by a fluid. The second sheet material 2184 may be, for example, rice paper. The second sheet material 2184 may be arranged between the first sheet material 2182 and a window 2112 in the body 2110 of the fluid verification module 2100. Prior to the administration line 2000 being primed, the second sheet material 2184 is in the opaque state, thereby obstructing view of the indicia 2183 on the first sheet material 2182, as shown in FIG. 12. Once priming fluid flows in the priming cavity 2170, the second sheet material 2184 absorbs the priming fluid and assumes the at least partially transparent state such that the indicia 2183 can be viewed through the second sheet material 2184 and via the window 2112, as shown in FIG. 13. Visibility of the indicia 2183 thus indicates to the user that the administration line 2000 has been primed and/or been used in a previous injection procedure.

Figure 14:
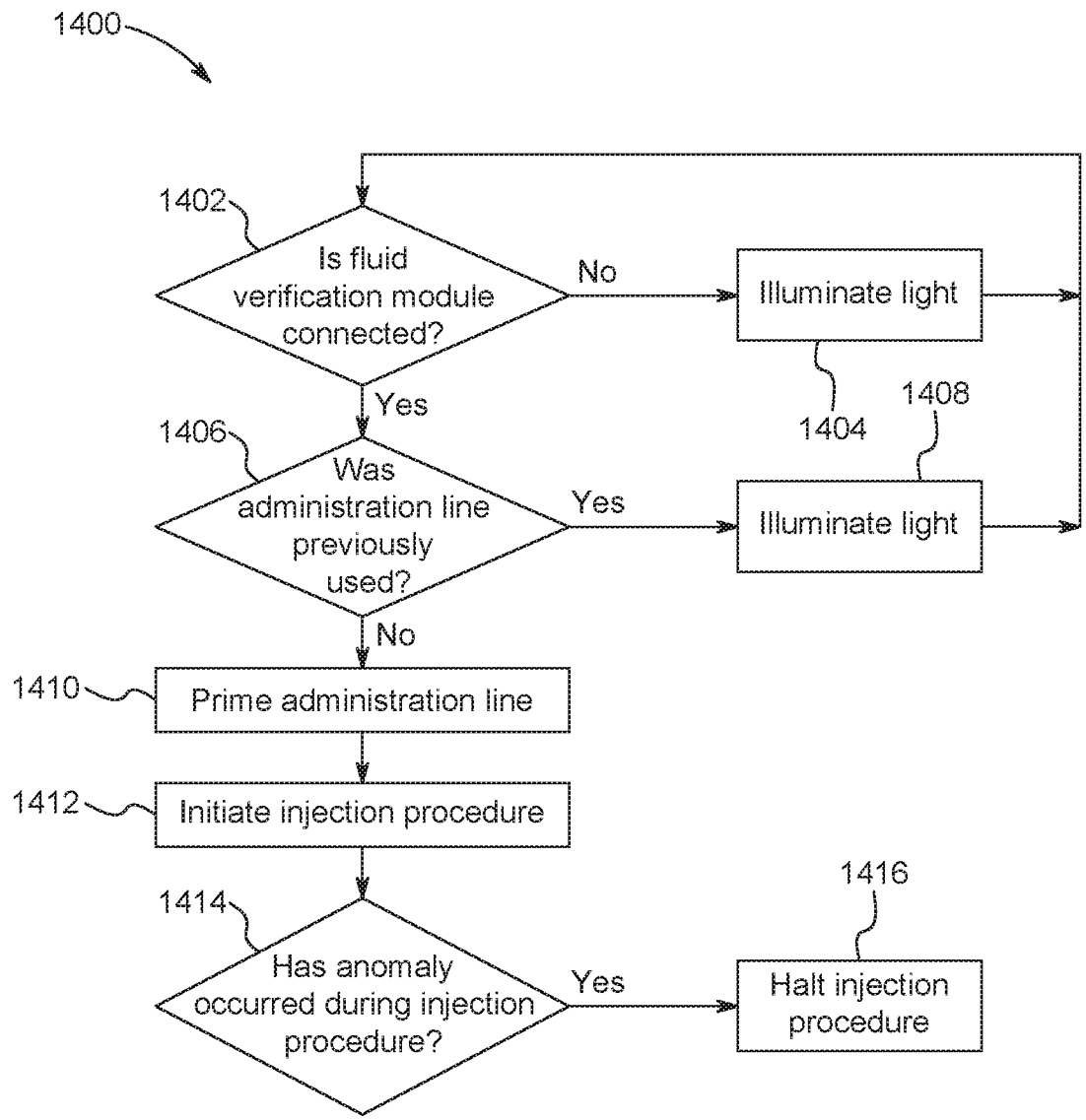
FIG. 14 is a flow diagram of a method of preparing a fluid injector system to perform an injection procedure in accordance with an aspect or example of the present disclosure.

Referring now to FIG. 14, a flow diagram for a method 1400 of preparing the fluid injector system 1000 to perform an injection procedure is shown. At step 1402, the method 1400 may include verifying that the fluid verification module 2100 is connected to the housing 15. In particular, the controller 900 may determine whether the one or more engagement features 162 of the mounting flange 16 are connected to the corresponding engagement features 2113 of the fluid verification model 2100. At step 1404, if the controller 900 determines that the fluid verification module 2100 is not properly connected to the housing 15, the controller 900 may illuminate the light source 164 in a first predetermined color and/or pattern to prompt the user to connect the fluid verification module 2100 to the housing 15. The controller 900 may then return to step 1402 to determine whether the fluid verification module 2100 has been properly connected to the housing 15.

At step 1406, if the fluid verification module 2100 is connected to the housing 15, the controller 900 may determine whether the administration line 2000 has been used in a previous injection procedure. In some aspects and examples, the controller 900 may use the probes 166 to measure the electrical resistance of the at least one sheet material 2180 to determine whether the at least one sheet material 2180 has absorbed fluid. In some aspects and examples, the controller 900 may use the at least one imaging device 169 to detect a color change of the at least one sheet material 2180 to determine whether the at least one sheet material 2180 has absorbed fluid. A determination that the at least one sheet material 2180 has absorbed fluid is indicative that the administration line 2000 has been used in a previous injection procedure. In some aspects and examples, the controller 900 may use an ultrasonic air detector to detect the presence or absence of air in the fluid verification module 2100 to determine whether the administration line 2000 has been used in a previous injection procedure. At step 1408, if the controller 900 determines that the administration line 2000 has been used in a previous injection procedure, the controller 900 may illuminate the light source 164 in a second predetermined color and/or pattern to prompt the user to dispose of the present administration line 2000 and connect an unused administration line 2000. The controller 900 may then return to step 1402 to determine whether the unused administration line 2000 has been connected.

In the aspects or examples of the fluid injector system 1000 shown in FIGS. 3, 5, and 6, the multi-patient intermediate tubing set 1200 may be intended for use in a predetermined number of injection procedures. For example, the multi-patient intermediate tubing set 1200 may be approved for use in up to five injection procedures. In these aspects or examples, the controller 900 may keep a running count of the number of injection procedures for which the multi-patient intermediate tubing set 1200 has been used, and, so long as the number of uses is less than the predetermined number, the controller 900 may proceed from step 1408. The controller 900 may count the number of injection procedures for which the multi-patient intermediate tubing set 1200 has been used by, for example, counting the number of priming operations performed by the fluid injection system 1000 since the multi-patient intermediate tubing set 1200 was connected to the housing 15. If the controller 900 determines that the multi-patient intermediate tubing set 1200 has been used for the predetermined number of approved injection procedures, the controller 900 may prevent a further injection procedure from being performed even though the administration line 2000 has been replaced.

At step 1410, if the controller 900 determines that the administration line 2000 has not been used in a previous injection procedure and the balance of the fluid injection system 1000 is ready for use, the controller 900 performs a priming operation. In particular, the controller 900 may actuate the at least one syringe 12 to inject a priming fluid (e.g. saline) through the administration line 2000. The controller 900 may illuminate the light source 164 in a third predetermined color and/or pattern to indicate that the priming operation is being performed. In some aspects or examples, the controller 900 may inject a predetermined volume of the priming fluid based on a known volume of the administration line 2000. In other aspects or examples, the controller 900 may use the at least one imaging device 169 to determine a type of administration line 2000 that is connected to the fluid injector system 1000, and, based on that determination, inject a predetermined volume of the priming fluid. For example, the at least one imaging device 169 may include a barcode reader or RFID reader to read a corresponding barcode or RFID chip on the fluid verification module 2100 which contains information such as the volume of the administration line 2000. The controller 900 may then inject a volume of the priming fluid in accordance with the information stored on the barcode or RFID chip. In other aspects or examples, the controller 900 may inject the priming fluid until the at least one sheet material 2180 absorbs the priming fluid, as determined using the probes 166 and/or the imaging device 169. Once the priming operation is complete, the controller 900 may illuminate the light source 164 in a fourth predetermined color and/or pattern to indicate that the fluid injector system 1000 is ready to perform an injection procedure.

At step 1412, the controller 900 may initiate performance of an injection procedure. The injection procedure may include a predetermined and/or preprogrammed volume and flow rate of one or more fluids from the at least one syringe 12. The controller 900 may illuminate the light source 164 in a fifth predetermined color and/or pattern to indicate that the injection procedure is in progress.

During performance of the injection procedure, at step 1414, the controller 900 may monitor the administration line 2000 to ensure patient safety and adherence to the injection procedure. In particular, the controller 900 may determine whether an anomaly occurs during the injection procedure. In some aspects or examples, the controller 900 may monitor the main fluid channel 2124, via the imaging device 169, for the presence of air. In some aspects or examples, the controller 900 may monitor the main fluid channel 2124, via the strain gauge 168, to determine the injection pressure. At step 1416, if air is detected in the main fluid channel 2124 and/or if another parameter monitored by the controller 900 is not within predetermined limits, the controller 900 may halt the injection procedure. The controller 900 may illuminate the light source 164 in a sixth predetermined color and/or pattern to indicate that the injection procedure has been halted.

Figure 15:
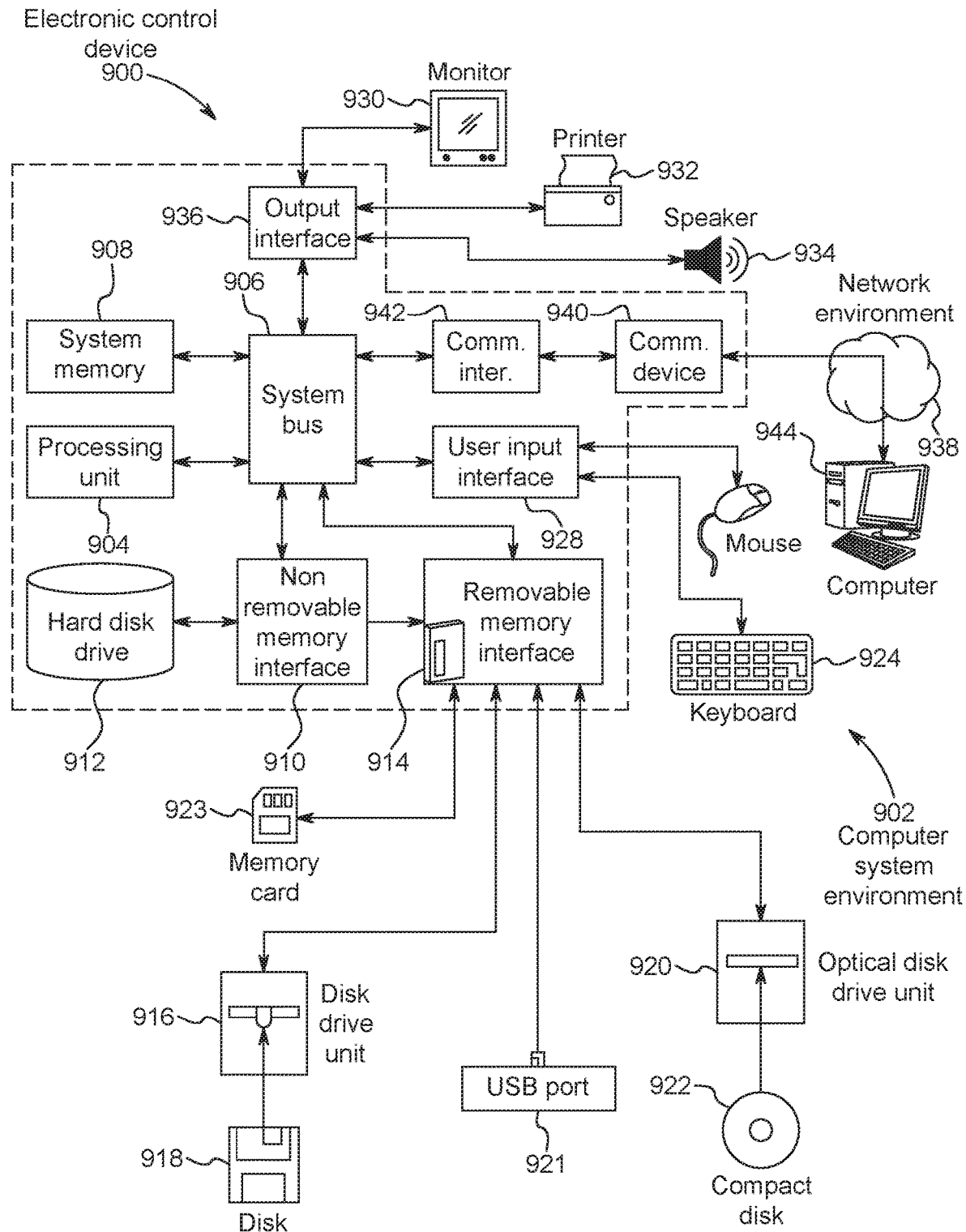
FIG. 15 is a schematic view of an electronic control system of a fluid injector system in accordance with an aspect or example of the present disclosure.

Referring now to FIG. 15, the electronic control device 900 may be associated with the fluid injector system 1000 to control the filling and delivery operations. In some examples, the electronic control device 900 may control the operation of various valves, piston members, and other elements to effect a desired filling or delivery procedure. For example, the electronic control device 900 may include a variety of discrete computer-readable media components. For example, this computer-readable media may include any media that can be accessed by the electronic control device 900, such as volatile media, non-volatile media, removable media, non-removable media, transitory media, non-transitory media, etc. As a further example, this computer-readable media may include computer storage media, such as media implemented in any method or technology for storage of information, such as computer-readable instructions, data structures, program modules, or other data; random access memory (RAM), read-only memory (ROM), electrically erasable programmable read-only memory (EEPROM), flash memory, or other memory technology; CD-ROM, digital versatile disks (DVDs), or other optical disk storage; magnetic cassettes, magnetic tape, magnetic disk storage, or other magnetic storage devices; or any other medium which can be used to store the desired information and which can be accessed by the electronic control device 900. Further, this computer-readable media may include communications media, such as computer-readable instructions, data structures, program modules, or other data in a modulated data signal, such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The electronic control device 900 further includes a system memory 908 with computer storage media in the form of volatile and non-volatile memory, such as ROM and RAM. A basic input/output system (BIOS) with appropriate computer-based routines assists in transferring information between components within the electronic control device 900 and is normally stored in ROM. The RAM portion of the system memory 908 typically contains data and program modules that are immediately accessible to or presently being operated on by a processor 904, e.g., an operating system, application programming interfaces, application programs, program modules, program data, and other instruction-based computer-readable codes.

With continued reference to FIG. 15, the electronic control device 900 may also include other removable or non-removable, volatile or non-volatile, transitory or non-transitory computer storage media products. For example, the electronic control device 900 may include a non-removable memory interface 910 that communicates with and controls a hard disk drive 912, e.g., a non-removable, non-volatile magnetic medium; and a removable, non-volatile memory interface 914 that communicates with and controls a magnetic disk drive unit 916 (which reads from and writes to a removable, non-volatile magnetic disk 918), an optical disk drive unit 920 (which reads from and writes to a removable, non-volatile optical disk 922, such as a CD ROM), a Universal Serial Bus (USB) port 921 for use in connection with a removable memory card, etc. However, it is envisioned that other removable or non-removable, volatile or non-volatile computer storage media can be used in an exemplary computing system environment 902, including, but not limited to, magnetic tape cassettes, DVDs, digital video tape, solid state RAM, solid state ROM, etc. These various removable or non-removable, volatile or non-volatile magnetic media are in communication with the processor 904 and other components of the electronic control device 900 via a system bus 906. The drives and their associated computer storage media, discussed above and illustrated in FIG. 15, provide storage of operating systems, computer-readable instructions, application programs, data structures, program modules, program data, and other instruction-based, computer-readable code for the electronic control device 900 (whether duplicative or not of this information and data in the system memory 908).

A user may enter commands, information, and data into the electronic control device 900 through certain attachable or operable input devices, such as a user interface on the housing 15, via a user input interface 928. A variety of such input devices may be utilized, e.g., a microphone, a trackball, a joystick, a touchpad, a touchscreen, a scanner, etc., including any arrangement that facilitates the input of data and information to the electronic control device 900 from an outside source. As discussed, these and other input devices are often connected to the processor 904 through the user input interface 928 coupled to the system bus 906, but may be connected by other interface and bus structures, such as a parallel port, game port, or a USB. Still further, data and information can be presented or provided to a user in an intelligible form or format through certain output devices, such as a monitor 930 (to visually display this information and data in electronic form), a printer 932 (to physically display this information and data in print form), a speaker 934 (to audibly present this information and data in audible form), etc. All of these devices are in communication with the electronic control device 900 through an output interface 936 coupled to the system bus 906. It is envisioned that any such peripheral output devices be used to provide information and data to the user.

The electronic control device 900 may operate in a network environment 938 through the use of a communications device 940, which is integral to the electronic control device 900 or remote therefrom. This communications device 940 is operable by and in communication with the other components of the electronic control device 900 through a communications interface 942. Using such an arrangement, the electronic control device 900 may connect with or otherwise communicate with one or more remote computers, such as a remote computer 944, which may be a personal computer, a server, a router, a network personal computer, a peer device, or other common network nodes, and typically includes many or all of the components described above in connection with the electronic control device 900. Using appropriate communication devices 940, e.g., a modem, a network interface or adapter, etc., the computer 944 may operate within and communicate through a local area network (LAN) and a wide area network (WAN), but may also include other networks such as a virtual private network (VPN), an office network, an enterprise network, an intranet, the Internet, etc.

As used herein, the electronic control device 900 includes or is operable to execute appropriate custom-designed or conventional software to perform and implement the processing steps of the method and system of the present disclosure, thereby forming a specialized and particular computing system. Accordingly, the method and system may include one or more electronic control devices 900 or similar computing devices having a computer-readable storage medium capable of storing computer-readable program code or instructions that cause the processor 904 to execute, configure, or otherwise implement the methods, processes, and transformational data manipulations discussed hereinafter in connection with the present disclosure. Still further, the electronic control device 900 may be in the form of a personal computer, a personal digital assistant, a portable computer, a laptop, a palmtop, a mobile device, a mobile telephone, a server, or any other type of computing device having the necessary processing hardware to appropriately process data to effectively implement the fluid injector system 1000, the computer program product and the computer-implemented method of the present disclosure.

It will be apparent to one skilled in the relevant arts that the system may utilize databases physically located on one or more computers which may or may not be the same as their respective servers. For example, programming software on the electronic control device 900 can control a database physically stored on a separate processor of the network or otherwise.

While examples of fluid injector systems, administration lines, and methods of operation thereof were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

The invention claimed is:

1. An administration line for use with a fluid injector system, the administration line comprising:
   a fluid verification module configured to be in operative communication with a housing of the fluid injector system such that the fluid injector system can determine a status of the administration line, the fluid verification module comprising:
      a body defining an inlet port, an outlet port, a fluid channel extending from the inlet port to the outlet port, and a priming port in fluid communication with a priming cavity;
   a first tubing section connected to the inlet port; and
   a second tubing section connected to the outlet port, wherein the second tubing section comprises an outlet fitting configured to connect to the priming port during storage or shipment of the administration line, and wherein the priming cavity is configured to receive and hold priming fluid from the outlet fitting during a priming operation of the administration line.

2. The administration line of claim 1, wherein the first tubing section comprises:
a first inlet fitting configured for connection to a first fluid reservoir of the fluid injector system; and
a second inlet fitting configured for connection to a second fluid reservoir of the fluid injector system,
wherein the first inlet fitting is configured to connect to the second inlet fitting during storage or shipment of the administration line.

3. The administration line of claim 1, wherein the first tubing section comprises:
an inlet fitting configured for connection to an intermediate tubing set in fluid communication with at least one fluid reservoir of the fluid injector system,
wherein the inlet fitting is configured to connect to the body of the fluid verification module during storage or shipment of the administration line.

4. The administration line of claim 1, further comprising at least one sheet material disposed within the priming cavity, the at least one sheet material comprising:
a first sheet material having indicia; and
a second sheet material which transitions from an opaque state to an at least partially translucent state when the second sheet material is contacted by the priming fluid,
wherein the indicia on the first sheet material is obstructed by the second sheet material when the second sheet material is in the opaque state, and
wherein the indicia on the first sheet material is visible via a window in the body when the second sheet material is in the translucent state.

5. The administration line of claim 1, further comprising at least one sheet material disposed within the priming cavity,
wherein the at least one sheet material is configured to change in electrical resistance when contacted by the priming fluid, and
wherein, when the fluid verification module is mounted to the housing of the fluid injector system, the at least one sheet material is configured to interface with at least one probe of the fluid injector system for measuring electrical resistance of the at least one sheet material.

6. The administration line of claim 1, wherein the body of the fluid verification module further comprises a capillary channel in fluid communication with the priming cavity and configured to take up at least a portion of the priming fluid via capillary action.

7. The administration line of claim 1, wherein at least a portion of the body of the fluid verification module is configured to act as a lens to display light emitted from a light source of the fluid injector system.

8. The administration line of claim 1, wherein the body of the fluid verification module comprises one or more engagement features configured for securing the fluid verification module to the housing of the fluid injector system.

9. The administration line of claim 1, wherein the fluid channel is at least partially transparent such that an imaging device of the housing can determine the presence or absence of fluid in the fluid channel.

10. The administration line of claim 1, wherein the fluid channel is flexible and configured to interface with a strain gauge of the housing such that the strain gauge can determine fluid pressure in the administration line.

11. The administration line of claim 1, further comprising at least one of:
an inlet one-way valve associated with the inlet port; and
an outlet one-way valve associated with the outlet port,
wherein at least one of the inlet one-way valve and the outlet one-way valve prohibit fluid flow in an upstream direction from the second tubing section toward the first tubing section.

12. A fluid injector system configured to perform an injection procedure in connection with a diagnostic imaging procedure, the fluid injector system comprising:
an administration line comprising:
a fluid verification module, the fluid verification module comprising a body defining an inlet port, an outlet port, a fluid channel extending from the inlet port to the outlet port, and a priming port in fluid communication with a priming cavity;
a first tubing section connected to the inlet port; and
a second tubing section connected to the outlet port, wherein the second tubing section comprises an outlet fitting configured to connect to the priming port during storage or shipment of the administration line, and wherein the priming cavity is configured to receive and hold priming fluid from the outlet fitting during a priming operation of the administration line; and
a controller programmed or configured to determine a status of the administration line.

13. The fluid injector system of claim 12, wherein the first tubing section comprises:
a first inlet fitting configured for connection to a first fluid reservoir of the fluid injector system; and
a second inlet fitting configured for connection to a second fluid reservoir of the fluid injector system,
wherein the first inlet fitting is configured to connect to the second inlet fitting during storage or shipment of the administration line.

14. The fluid injector system of claim 12, wherein the first tubing section comprises:
an inlet fitting configured for connection to an intermediate tubing set in fluid communication with at least one fluid reservoir of the fluid injector system,
wherein the inlet fitting is configured to connect to the body of the fluid verification module during storage or shipment of the administration line.

15. The fluid injector system of claim 12, further comprising:
at least one probe for measuring electrical resistance in communication with the controller; and
at least one sheet material disposed within the priming cavity,
wherein the at least one sheet material is configured to change in electrical resistance when contacted by the priming fluid, and
wherein the controller is programmed or configured to prohibit performance of an injection procedure in response to determining, via the at least one probe, that the at least one sheet material has been previously contacted by the priming fluid.

16. The fluid injector system of claim 12, further comprising an imaging device in communication with the controller,
wherein the fluid channel is at least partially transparent such that the controller can determine the presence or absence of fluid in the fluid channel via the imaging device; and
wherein the controller is programmed or configured to halt performance of a fluid injection procedure in response to detecting air in the fluid channel via the imaging device.

* * * * *

UNITED STATES PATENT AND TRADEMARK OFFICE
CERTIFICATE OF CORRECTION

PATENT NO. : 12,311,158 B2
APPLICATION NO. : 17/639641
DATED : May 27, 2025
INVENTOR(S) : John Volkar Page 1 of 1

It is certified that error appears in the above-identified patent and that said Letters Patent is hereby corrected as shown below:

In the Specification

In Column 1, Line 11, delete "is are" and insert -- are --, therefor.

In Column 6, Line 2, delete "port." and insert -- port, --, therefor.

In Column 7, Line 46, delete "position." and insert -- position; --, therefor.

In Column 7, Line 56, delete "detail" and insert -- detailed --, therefor.

In Column 11, Line 31, delete "outer" and insert -- outlet --, therefor.

In Column 14, Line 5, delete "of portion" and insert -- a portion --, therefor.

In Column 19, Line 13, delete "CD ROM)," and insert -- CD-ROM), --, therefor.

Signed and Sealed this
Fifteenth Day of July, 2025

Coke Morgan Stewart
*Acting Director of the United States Patent and Trademark Office*